(12) United States Patent (10) Patent No.: US 10,054,535 B2
Mueller (45) Date of Patent: Aug. 21, 2018

(54) METHOD AND DEVICE FOR DETERMINING THE ORIENTATION OF PIGMENT PARTICLES OVER AN EXTENDED REGION OF AN OPTICALLY EFFECT LAYER

(71) Applicant: SICPA HOLDING SA, Prilly (CH)

(72) Inventor: Edgar Mueller, Lausanne (CH)

(73) Assignee: SICPA HOLDING SA, Prilly (CH)

( * ) Notice: Subject to any disclaimer, the term of this patent is extended or adjusted under 35 U.S.C. 154(b) by 358 days.

(21) Appl. No.: 14/909,205

(22) PCT Filed: Jul. 25, 2014

(86) PCT No.: PCT/EP2014/066051
§ 371 (c)(1),
(2) Date: Feb. 1, 2016

(87) PCT Pub. No.: WO2015/014748
PCT Pub. Date: Feb. 5, 2015

(65) Prior Publication Data
US 2016/0216194 A1 Jul. 28, 2016

(30) Foreign Application Priority Data
Aug. 2, 2013 (EP) .................................. 13179135

(51) Int. Cl.
*H04N 7/18* (2006.01)
*G01N 15/14* (2006.01)
(Continued)

(52) U.S. Cl.
CPC ......... *G01N 15/1434* (2013.01); *G01B 11/14* (2013.01); *G01N 21/4738* (2013.01);
(Continued)

(58) Field of Classification Search
CPC ............... G01N 21/4738; G01N 21/55; G01N 2021/4771; G01N 2021/4783;
(Continued)

(56) References Cited

U.S. PATENT DOCUMENTS 2,570,856 A 10/1951 Carlton et al.
3,676,273 A 7/1972 Graves
(Continued)

FOREIGN PATENT DOCUMENTS

EP 0087222 A2 8/1983
WO WO2002090002 A2 11/2002
(Continued)

OTHER PUBLICATIONS

Schindelin et al., "Fiji: an open-source platform for biological-image analysis," Nature Methods, vol. 9, No. 7, pp. 676-682 (Jun. 28, 2012).

*Primary Examiner* — Sathyanaraya V Perungavoor
*Assistant Examiner* — Peet Dhillon
(74) *Attorney, Agent, or Firm* — Muncy, Geissler, Olds & Lowe, P.C.

(57) ABSTRACT

Disclosure relates to a method and a device for determining the distribution and orientation of platelet-shaped pigment particles over an extended region of an optical effect layer (OEL). The method includes a) taking at least one image, under illumination of said extended region of the optical effect layer with collimated light incident from at least one first direction, of reflected light of said extended region of the optical effect layer from at least one second direction, using a telecentric lens-and-camera assembly having the optical axis of the telecentric lens oriented along said second direction, and b) processing the at least one image of said extended region to extract quantitative particle distribution and orientation information. The device includes a) a colli- (Continued)

mated light source for illuminating an extended region of the optical effect layer with collimated light from at least one first direction, and b) a telecentric lens-and-camera assembly for collecting the light reflected from said extended region of the optical effect layer into at least one second direction.

21 Claims, 11 Drawing Sheets

(51) Int. Cl.
| | |
|---|---|
| *G01N 21/47* | (2006.01) |
| *G01N 21/55* | (2014.01) |
| *G01B 11/14* | (2006.01) |
| *G07D 7/121* | (2016.01) |
| *G07D 7/20* | (2016.01) |

(52) U.S. Cl.
CPC .............. *G01N 21/55* (2013.01); *G07D 7/121* (2013.01); *G07D 7/2016* (2013.01); *G01N 2015/144* (2013.01); *G01N 2021/4771* (2013.01); *G01N 2021/4783* (2013.01)

(58) Field of Classification Search
CPC ......... G01N 15/1434; G01N 2015/144; G07D 7/121; G07D 7/2016; G01B 11/14
See application file for complete search history.

(56) References Cited

U.S. PATENT DOCUMENTS

| | | | |
|---|---|---|---|
| 3,791,864 A | 2/1974 | Steingroever | |
| 5,364,689 A | 11/1994 | Kashiwagi et al. | |
| 5,630,877 A | 5/1997 | Kashiwagi et al. | |
| 7,276,719 B2* | 10/2007 | Schwarz ................. | G01J 3/50 |
| | | | 250/223 R |
| 7,483,127 B1* | 1/2009 | Li ............................. | G01J 3/02 |
| | | | 356/237.1 |
| 2005/0083529 A1 | 4/2005 | Vogel et al. | |
| 2005/0106367 A1 | 5/2005 | Raksha et al. | |

FOREIGN PATENT DOCUMENTS

| | | |
|---|---|---|
| WO | WO2005002866 A1 | 1/2005 |
| WO | WO2007018727 A1 | 2/2007 |

* cited by examiner

METHOD AND DEVICE FOR DETERMINING THE ORIENTATION OF PIGMENT PARTICLES OVER AN EXTENDED REGION OF AN OPTICALLY EFFECT LAYER

CROSS-REFERENCE TO RELATED APPLICATIONS

The present application is a National Stage Application of International Application No. PCT/EP2014/066051 filed Jul. 25, 2014, which published as WO 2015/014748 A1 on Feb. 5, 2015, the disclosures of which are expressly incorporated by reference herein in their entireties. Further, the present application claims priority to European Application No. 13179135.2, filed Aug. 2, 2013, the disclosure of which is expressly incorporated by reference herein in its entirety.

BACKGROUND OF THE DISCLOSURE

1. Field of the Disclosure

The present disclosure relates to the field of the protection of security documents and more particularly to a method and a device for determining the distribution and orientation of platelet-shaped pigment particles over an extended region of an optical effect layer. The optical effect layer may be a constituent of a bank note, credit card or other security document. The platelet-shaped pigment particles are preferably non-diffractive particles, i.e., platelet-shaped pigment particles having no diffractive surface structure.

2. Background Description

It is known in the art to use inks, compositions or layers containing oriented magnetic or magnetizable particles or pigments, particularly also optically variable magnetic or magnetizable pigments, for the production of security elements, e.g. for security documents. Coatings or layers comprising oriented magnetic or magnetizable particles are disclosed for example in U.S. Pat. No. 2,570,856; U.S. Pat. No. 3,676,273; U.S. Pat. No. 3,791,864; U.S. Pat. No. 5,630,877 and U.S. Pat. No. 5,364,689. Coatings or layers comprising oriented magnetic color-shifting pigment particles, resulting in particularly appealing optical effects, useful for the protection of security documents, have been disclosed in WO 2002/090002 A2 and WO 2005/002866 A1. U.S. Pat. No. 7,276,719 B2 discloses a device for a goniometric examination of optical properties of a surface comprising at least one first radiation device at a predetermined spatial angle to a surface to be examined and a detector device for capturing the radiation emitted to and reflected back from the surface. US 2005/083529 A1 discloses a method and apparatus for determining the effect-particle orientation in a film or coating. In EP 0 087 222 A2, an apparatus and method for characterizing surface coating films is disclosed. WO 2007/018727 discloses a method and an apparatus for imaging a target area wherein a target area is illuminated with collimated light and light reflected from the target area is collected by a telecentric lens and camera system.

Although methods and systems for producing such layers are known in the art, little is still known about the distribution and the specific orientation of the pigment particles over an extended region in said layer. There is also a need to better understand the kinetics of the particles' orientation during the production process of said layer, which depends in part on the local direction and strength of the applied magnetic field, on the relative movements of the layer and the magnets, on the viscosity of the unhardened coating composition and/or on the time scale of the production process.

The main existing tool to gain insight into the particle orientation over an extended region of a hardened coating layer is the electron-microscopic (e.g., SEM) examination of representative cuts through the coating layer. This method is rather tedious, because of the required particular sample preparation, the large number of SEM pictures required to characterize an entire security element and the high amount of data to be processed and analyzed. Furthermore, with this approach the sample under investigation is destroyed in the process.

Therefore, there is a need for a device and a non-destructive method for characterizing the distribution and orientation of pigment particles over an extended region of said layer in a less tedious way. The device should, in particular, be useful for characterizing the distribution and orientation of platelet-shape particles in a layer, e.g., platelet-shape optical variable pigment particles. In particular, the device should be useful for characterizing security elements on documents such as bank notes, etc., which were produced by orienting magnetic or magnetizable particles or pigments, particularly optically variable magnetic or magnetizable pigments in an applied layer, followed by hardening said layer, such as to freeze the pigment particles in their adopted positions and orientations.

SUMMARY OF THE DISCLOSURE

Accordingly, it is an aim of the present disclosure to provide a method and a device for efficiently and accurately determining the distribution and orientation of platelet-shaped pigment particles over an extended region of an optical effect layer (OEL) comprising said pigment particles.

The method according to the present disclosure for determining the distribution and orientation of platelet-shaped pigment particles, in particular platelet-shaped optically variable magnetic or magnetizable pigment particles, over an extended region of an optical effect layer comprising said pigment particles comprises:

a) taking at least one image, under illumination of said extended region of the optical effect layer with collimated light incident from at least one first direction, of reflected light of said extended region of the optical effect layer from at least one second direction, using a telecentric lens-and-camera assembly having the optical axis of the telecentric lens oriented along said second direction, and b) processing the at least one image of said extended region to extract quantitative particle distribution and orientation information.

Also described and claimed herein are devices for determining the distribution and orientation of platelet-shaped pigment particles, in particular platelet-shaped optically variable magnetic or magnetizable pigment particles, over an extended region of an optical effect layer comprising said pigment particles, and uses of said devices for carrying out the method described herein, such device comprising:

a) a collimated light source for illuminating an extended region of the optical effect layer with collimated light from at least one first direction, and b) a telecentric lens-and-camera assembly for collecting the light reflected from said extended region of the optical effect layer into at least one second direction, wherein an optical axis of the telecentric lens-and-camera assembly is oriented along said second direction and the telecentric lens-and-camera assembly is configured for taking at least one image, under illumination of the extended region of the optical effect layer with the collimated light incident from the first direction, of the light reflected from the extended region of the optical effect layer from the second direction, and c) a processor for processing the at least one image of the extended region to extract quantitative particle distribution and orientation information.

BRIEF DESCRIPTION OF THE DRAWINGS

The devices and methods according to the present disclosure are now described in more detail with reference to the drawings and to particular embodiments, wherein.

DETAILED DESCRIPTION OF EMBODIMENTS OF THE DISCLOSURE

Definitions

Figure 1:
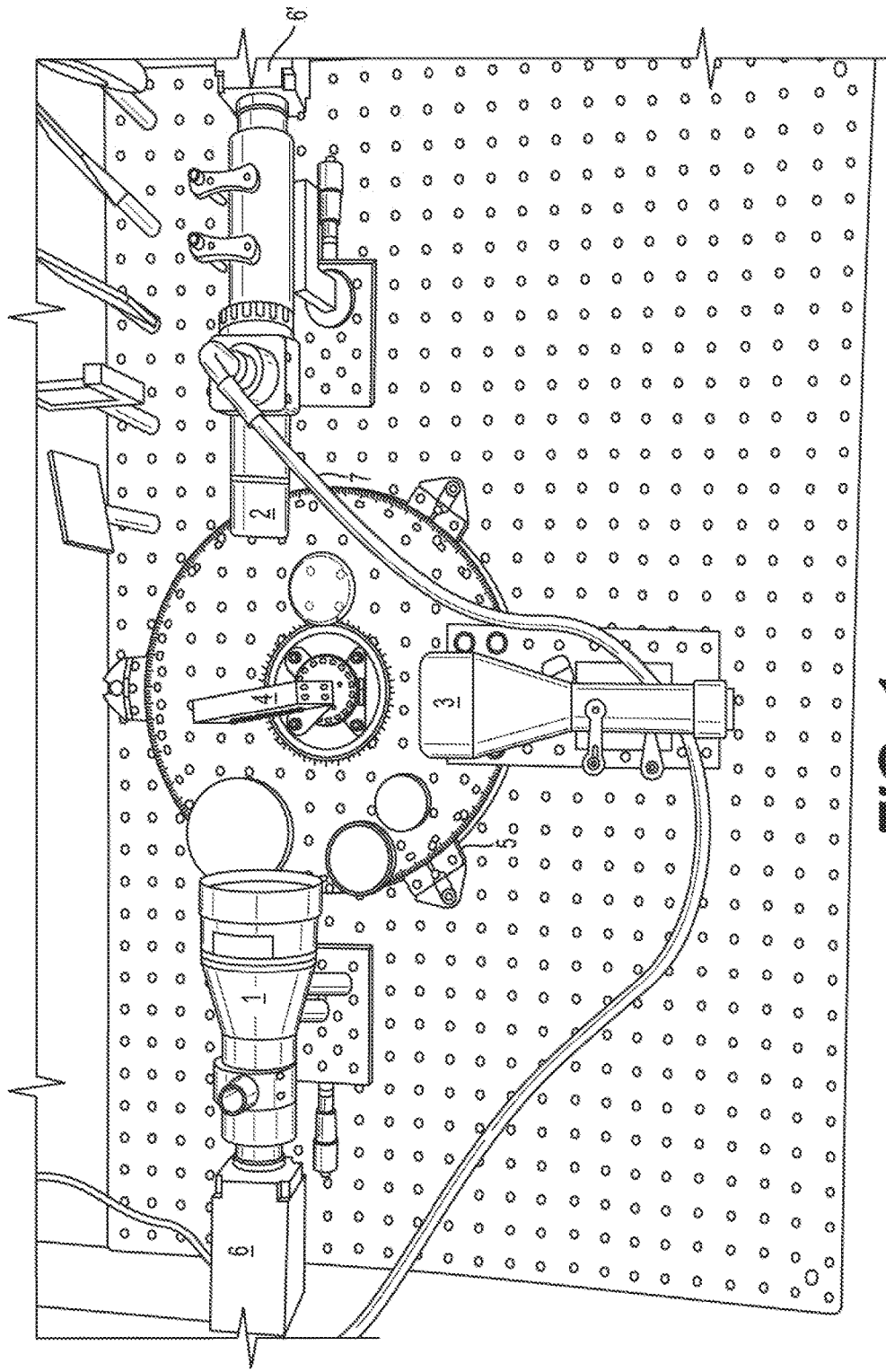
FIG. 1 is a top-view drawing of an exemplary set-up of a device according to the present disclosure.

The following definitions shall be used to interpret the meaning of the terms discussed in the description and recited in the claims.

As used herein, the indefinite article "a" indicates one as well as more than one and does not necessarily limit its referent noun to the singular.

As used herein, the term "about" indicates that the amount or value in question may be the specific value designated or some other value in its neighborhood. Generally, the term "about" denoting a certain value is intended to denote a range within +5% of the value. As one example, the phrase "about 100" denotes a range of 100±5, i.e. the range from 95 to 105. Generally, when the term "about" is used, it can be expected that similar results or effects according to the disclosure can be obtained within a range of ±5% of the indicated value.

As used herein, the term "and/or" indicates that either all or only one of the elements of said group may be present. For example, "A and/or B" shall mean "only A, or only B, or both A and B". In the case of "only A", the term also covers the possibility that B is absent, i.e. "only A, but not B".

The term "substantially parallel" refers to deviating less than 20° from parallel alignment and the term "substantially perpendicular" refers to deviating less than 20° from perpendicular alignment. The term "parallel" refers to deviating less than 5° from mathematically exact parallel alignment. Similarly "perpendicular" refers to deviating less than 5° from mathematically exact perpendicular alignment.

The term "at least partially" is intended to denote that the following property is fulfilled to a certain extent or completely.

The terms "substantially" and "essentially" are used to denote that the following feature, property or parameter is either completely (entirely) realized or satisfied or to a major degree that does not adversely affect the intended result.

The term "comprising" as used herein is intended to be non-exclusive and open-ended. Thus, for instance a coating composition comprising a compound A may include other compounds besides A. However, the term "comprising" also covers the more restrictive meanings of "consisting essentially of" and "consisting of", so that for instance "a coating composition comprising a compound A" may also (essentially) consist of the compound A.

The term "coating composition" refers to any composition that is capable of forming an optical effect layer (OEL) of the present disclosure on a solid substrate, and which can be applied preferentially but not exclusively by a printing method. The coating composition comprises at least platelet-shaped pigment particles and a binder to hold the pigment particles in place, i.e. in position and orientation, after hardening. Due to their non-spherical shape, the particles have non-isotropic reflectivity.

The term "optical effect layer (OEL)" as used herein denotes a layer that comprises platelet-shaped pigment particles and a binder, wherein the orientation of the pigment particles is fixed within the binder. The platelet-shaped pigment particles are known in the art as "effect pigments", i.e. structures imparting a directional light reflectance, scattering, absorption, or optically variable appearance to the substrate in or on which they are applied.

An "extended region" as used herein denotes a region at least as large as to statistically support more than one local orientation of pluralities of platelet-shaped pigment particles.

"Collimated light" as used herein denotes a light beam whose rays are nearly parallel, so that the beam does not substantially converge or diverge.

"Telecentric lens" as used herein denotes a lens producing an image of an object from essentially parallel light.

"Taking an image" as used herein denotes a point-to-point mapping of the surface of the imaged object to the image surface, i.e. the image shall be taken in focused conditions, i.e. be a photographic image.

Figure 3A:
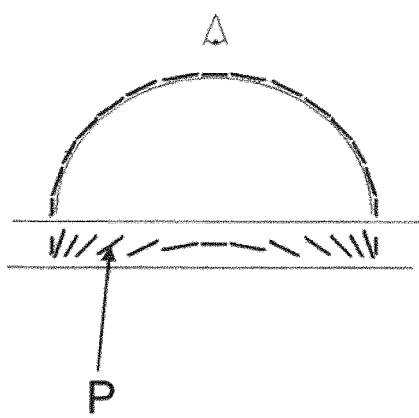
FIG. 3A schematically illustrates a coating comprising platelet-shaped pigment particles (P) oriented such as to produce a negative "rolling bar" effect.
Figure 3B:
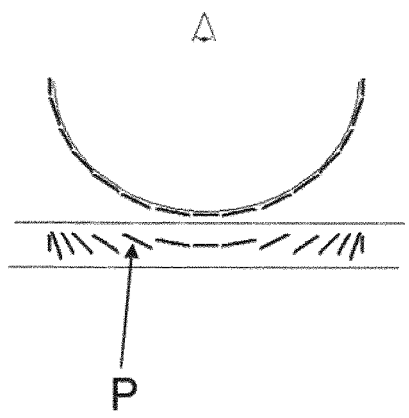
FIG. 3B schematically illustrates a coating comprising platelet-shaped pigment particles (P) oriented such as to produce a positive "rolling bar" effect.

The term "rolling bar" or "rolling bar effect" denotes an area within the OEL that provides the optical effect or optical impression of a half-cylindrical bar shape. The observer sees a specular reflection zone that moves away or towards the observer as the image is tilted. The "rolling bar", i.e. the half-cylindrical bar shape, can be symmetrical or non-symmetrical. Examples of "rolling bar" effects are illustrated in FIGS. 3A and 3B, wherein platelet-shaped pigment particles P are oriented according to a negative "rolling bar" effect (FIG. 3A) or according to a positive "rolling bar" effect (FIG. 3B).

The term "security element" or "security feature" is used to denote an image or graphic element that can be used for authentication purposes. The security element or security feature can be an overt and/or a covert security element.

In one aspect, the present disclosure provides a method for determining the distribution and orientation of platelet-shaped pigment particles, in particular platelet-shaped optically variable magnetic or magnetizable pigment particles, over an extended region of an OEL comprising said pigment particles, the method comprising:

a) taking at least one image, under illumination of said extended region of the OEL with collimated light incident from at least one first direction, of light reflected from said extended region of the OEL into at least one second direction, by using a telecentric lens-and-camera assembly having the optical axis of the telecentric lens oriented along said second direction, and b) processing the at least one image of said extended region to extract quantitative particle distribution and orientation information.

The method according to the present disclosure allows for efficiently and accurately determining the distribution and orientation of platelet-shaped pigment particles over an extended region of an OEL comprising said pigment particles. The OEL to be analyzed is hereto held in place in a defined orientation. The OEL has a substantially planar shape and the orientation of the planar OEL can be set, e.g., by a holder, a conveyor or similar arrangement, by which the OEL is held or placed in its defined orientation.

The OEL to be analyzed and placed in the defined orientation is illuminated with collimated light from the collimated light source from at least one first direction, and an image of the light reflected into at least one second direction by said extended region of the OEL is collected with the help of the telecentric lens and camera assembly. Only light reflected by particularly oriented platelet-shaped pigment particles into the direction of the axis of the telecentric lens will contribute to the image formed, which means that only those pigment particles will be visible in the image, whose surface normals are oriented along the angle bisector (also referred as bisecting line B) between the illumination direction and the telecentric lens optical axis direction (i.e., pigment particles oriented in specular reflection condition). The image shows then where the pigment particles having that specific orientation are located in the OEL.

The collimated light is thus directed onto and received from the OEL at specific angles of incidence, from which the orientation of the reflecting platelet-shaped pigment particle can be deduced. If the illuminating light source is not collimated, it is not possible to determine the orientation of the platelet-shaped pigment particle, because the angle of incidence of the incoming light is unknown. The required collimated light can be provided by a collimating lens or by any light source which is operable to emit collimated light. A laser is also a collimated light source that can be used in the context of the present disclosure.

The collecting of reflected light from a second direction is realized such that only light, which travels along a predetermined direction, the second direction, is collected, while light travelling in other directions is disregarded. By limiting both the illumination and the collection of light to a first and a second direction, respectively, it is assured that the collected light was reflected from a plane having a specific, specular orientation with respect to said first and said second directions. Combining the knowledge of the orientation of the OEL and the measured orientation of the reflecting platelet-shaped pigment particles, information about the relative orientations of the reflecting pigment particles with respect to the OEL can be deduced. The collected light is reconstructed into an image by the telecentric lens and captured with a camera or image sensor, and it is thus possible to not only measure whether light is reflected from the OEL, i.e. whether there are platelet-shaped pigment particles that are oriented accordingly within the OEL, but also to record the distribution of reflecting platelet-shaped pigment particles over the surface of the OEL for said orientation of the OEL. By this method, it is possible to measure the amount of platelet-shaped pigment particles which are oriented in a specific orientation relative to the OEL. This relative orientation, which can be measured by the above method, is determined by the orientation of the OEL as well as the first and second directions of the illuminating light and the collected light, respectively.

A particularly simple case arises if said second direction, i.e. the imaging direction, is the same as said first direction, i.e. the illuminating direction. Such can be achieved by using a telecentric lens with on-axis illuminator. In such lens, the illuminating light is coupled, via a beam-splitter, into the optical imaging path, giving the lens the additional function of a collimated light illuminator. Images taken under such condition show only those platelet-shaped pigment particles of the OEL, whose reflecting face is orthogonal to the optical imaging axis, i.e., which have their surface normals oriented along the optical axis of the telecentric lens.

The collecting of reflected light from said second direction is realized with the help of a telecentric lens, whose optics only admits light that travels within a narrow angle along the direction of its axis, while light travelling in other directions is disregarded. By limiting both, the illumination and the collection light cones to narrow angles, the plane of the reflecting platelet-shaped pigment particle is defined within a narrowly determined, specific orientation.

The system for orienting the collimated light source, the telecentric lens-and-camera assembly, and the OEL is characterized by the three independent degrees of freedom: said first direction or collimated illumination direction, said second direction of the optical axis of the telecentric lens, corresponding to the azimuth angle ($\alpha$) of the OEL, and a further, out-of-plane elevation angle ($\eta$) of the OEL. To define the general measurement conditions, these three angles must be set. Preferably, the angle between illumination and observation is preset, and only the azimuth and/or elevation angles of the OEL are varied during a measurement sequence. Most preferably, the illumination- and observation angles are the same, as is the case with on-axis illumination. This is particularly interesting because only the orientation of the OEL is then changed as the method is carried out.

Considered from a general point of view, the information contained in a two-dimensional extended region of an OEL comprising platelet-shaped pigment particles is a four-dimensional manifold: the pigment particles can have a density distribution across the x-y plane of the OEL, and each pigment particle can be oriented in azimuth and elevation with respect to x-y plane of the OEL.

In the image processing step, the images must normally first be corrected for background light and other background effects, before the image data can be evaluated. To achieve this, an image of a completely light-absorbing background is taken with the telecentric lens-and-camera assembly under the same illumination and exposure conditions. This background image is then subtracted, prior to all further processing, from the images to be processed. Background light is always present when working with the on-axis illumination telecentric lens, because some light is necessarily Fresnel-reflected at the optical elements ahead of the beam splitter acting as the coupling mirror. Other background effects include the dark current of the camera, which can also be compensated in this way.

The (x,y)-images taken at various azimuth ($\alpha$) and elevation ($\eta$) angles are preferably further compensated for perspective distortion, to cover the same area in the further processing. This is easily achieved by stretching the images in the x and in the y directions by $(1/\cos(\alpha))$ and $(1/\cos(\eta))$ factors, respectively. Azimuth ($\alpha$) is herein the rotation effectuated from normal position around the y-axis, and elevation ($\eta$) is the rotation effectuated from normal position around the x-axis of the OEL.

The method according to the present disclosure comprises a step b) of processing the at least one image of said extended region to extract quantitative pigment particle distribution and orientation information. By combining, with the help of an appropriate mathematical model, the distribution of reflecting platelet-shaped pigment particle on the images with the corresponding orientations of the OEL, quantitative information about the distribution and orientation of the reflecting pigment particles across the OEL can be obtained.

The step of b) processing the at least one image can, for example, be achieved by forming one-dimensional or two-dimensional images of the collected light, where bright dots correspond to positions or coordinates where light of a high intensity is reflected. The images may also be processed and presented as a function of the azimuth ($\alpha$) and/or elevation ($\eta$) angles of the OEL; the amount of collectable information spans out a 4-dimensional space $(x,y,\alpha,\eta)$. Further, it is possible to illustrate the intensity of the collected light by vectors or any other numerical quantifier. The step c) of processing the at least one image of said extended region may therefore comprises one-dimensional or two-dimensional curve fitting to an image feature; one-dimensional or two-dimensional mathematical models may be fitted to image features in the processing step, using a least-squares algorithm, as known in the art, in order to obtain quantitative particle orientation information.

The step of b) processing may comprise an intensity integration or summation of the platelet-shaped pigment particles along one image axis, in order to obtain an integrated or cumulated intensity (or particle) distribution function along the other image axis. Such distribution function may show a maximum, whose intensity and/or position and/or width may represent the sought quantitative particle orientation information. Advantageously, such intensity or position or width of an intensity maximum is evaluated as a function of the rotation angles of the OEL in azimuth and/or elevation with respect to the optical axis of the telecentric lens, to extract the quantitative particle distribution and orientation information contained in the OEL.

An intensity-filtering of the at least one image can be applied in the processing step, in order to isolate the strongly reflecting pigment particles, which were imaged in specular reflection condition, from the weakly reflecting rest of the image. In such a way, the images can be transformed into a black (=no particle there) and white (=particle there) halftone information. Similarly, a color-filtering of the at least one image can be applied in the processing step, in order to isolate pigment particles of a determined color from the rest of the image.

Advantageously, a position or coordinate of a maximum intensity of the collected light in the two-dimensional image is determined, wherein preferably the position or coordinate of the maximum intensity of the collected light is set in relation to the orientation of the OEL at which the light was collected. The position of the maximum intensity or the coordinate of the maximum intensity may be of particular interest for measuring OEL comprising systematically distributed and oriented platelet-shaped pigment particles. The positions or coordinates of the maximum intensity of the collected light correspond to the positions of platelet-shaped pigment particles which most efficiently reflect the incident light into the second direction at those angular setting. This, in turn, means that the positions or coordinates of the maximum intensity of the collected light corresponds to those platelet-shaped pigment particles which are oriented in a specific way. Depending on the angle of incidence, the direction of collecting the reflected light and the orientation of the OEL, the relative orientation of the platelet-shaped pigment particles corresponding to the maximum intensity positions can be accurately determined.

In a preferred method, an intensity of the collected light is integrated, wherein preferably the integrated light intensity of the collected light is set in relation to the orientation of the OEL at which the light was collected. In other words, the total intensity of collected light is measured and preferably set in relation to the orientation of the OEL. This results in measuring the amount of platelet-shaped pigment particles which are oriented such that light of the set angle of incidence is reflected into the second direction, i.e. the direction of the collected light.

Advantageously, the obtained image is compensated for perspective distortion depending on azimuth and elevation angles of the OEL with respect to the axis of the telecentric lens. This compensation is particularly useful, if several images are taken at different azimuth and elevation angles and if these images have then to be superposed. Accordingly, compensating for the perspective distortion allows preserving the distances in the measured images, even if these are taken over a wide range of azimuth and elevation angles.

The method according to the present disclosure may further comprise a step of c) tilting the OEL with respect to the first orientation so that the plane of said extended region of the OEL is rotated in azimuth and/or elevation with respect to the optical axis of the telecentric lens, wherein steps a) and b) are carried out after the OEL being tilted. The OEL is thereby tilted by a predefined angle which can be chosen by an operator. This allows for an angularly resolved measurement in azimuth and/or elevation directions. In other words, one image can be taken for each orientation of the OEL. The first axis then defines a plane of rotation in which the angular resolution is available. The steps c) of tilting the OEL can preferably be carried out successively a plurality of times.

In another aspect, the present disclosure provides devices configured to produce a image of an extended region of an OEL which comprises oriented platelet-shaped pigment particles, in particular platelet-shaped optically variable magnetic or magnetizable pigment particles, in a hardened coating composition, wherein only those pigment particles having a determined orientation with respect to the optical axis of the imaging device appear in the photographic image. The device is configured to produce a graphical representation of the platelet-shaped pigment particles' orientation across a cross-section of an OEL produced by the orientation of platelet-shaped pigment particles, in particular, platelet-shaped optically variable magnetic or magnetizable pigment particles.

The device for determining the distribution and orientation of platelet-shaped pigment particles, in particular platelet-shaped optically variable magnetic or magnetizable pigment particles, over an extended region of an OEL comprising said pigment particles comprises:
a) a collimated light source for illuminating an extended region of the OEL with collimated light from at least one first direction,
b) a telecentric lens-and-camera assembly for collecting the light reflected from said extended region of the OEL into at least one second direction.

The collimated light can be provided by a collimating lens or by a light source that is operable to emit collimated light. A laser is a possible collimated light source which can be used in the present disclosure.

The collimated light source may be chosen from the broad-band and the narrow-band light sources, comprising incandescent light sources, discharge tube light sources, fluorescent light, Light-Emitting Diodes (LED), and lasers. The primarily interesting wavelength range of the light source is in the visible spectrum (400 nm to 700 nm), but light sources operating in the extended range in between 200 nm and 2500 nm may also be considered for particular applications. The collimated light source may furthermore be optically filtered with color filters (wavelength filters) and/or polarization filters.

The light source producing the collimated light may be configured for on-axis illumination or for off-axis illumination. In a particular embodiment, the telecentric lens is equipped with on-axis illuminator, for illuminating and taking the image from the same direction, i.e. where the first and said second directions described herein are the same.

The device according to the present disclosure comprises a telecentric lens-and-camera assembly for collecting the light reflected from said extended region of the OEL into at least one second direction. The camera can be chosen from the black-and-white cameras and from the color cameras; preferred color cameras are those using a Bayer-type color RG/GB color pattern composed of pixel quadruplets having one red, two green and one blue sensor pixel. Preferably, the camera is chosen from the cameras sensitive in the visible range (400 nm to 700 nm) but may optionally be sensitive in a more extended spectral wavelength range comprised within 200 nm and 2500 nm wavelength. The camera may furthermore be equipped with color filters (wavelength filters) and/or polarization filters.

The camera described herein is preferably an electronic image sensor of the CMOS or CCD type, and has typically a resolution of the order of 1.3 MPixel or more, and a global shutter. The image definition, i.e. how many μm of the specimen surface correspond to a pixel of the camera, is defined by pixel-size p of the image sensor and the magnification factor g of the telecentric lens, and is distance-independent.

Because a telecentric lens cannot image objects outside its own front-lens diameter D, the maximum size of the image sensor is given by $D*g$, and the pixel size p of the image sensor cannot be made arbitrarily small—it is typically of the order of 5 μm—hence the resolution at the specimen surface is given by $p/g$, and the maximum number of pixels supported along one dimension is $D*g/p$.

The collimated light source and the telecentric lens ensure that the first and second directions are narrowly defined and, thereby, ensure that the positions of the platelet-shaped pigment particles appearing in the image are really those of pigment particles oriented in specular position with respect to said first and second directions.

The present disclosure relates to a device comprising a telecentric lens. Telecentric lenses have very small acceptance angles, and construct the image using almost exclusively light rays which are parallel to the optical axis of the lens. A small acceptance angle, typically of the order of ±1° is, however, always needed, as no image can be constructed from absolutely parallel rays. Telecentric lenses have become widely used for optical devices useful for the precise measurement of physical distance, because they don't induce perspective-related and other image distortion. Telecentric lenses reduce or cancel-out most of the weaknesses of optical devices using other optics such as image distortion, perspective errors, and poor image resolution. Telecentric lenses are particularly useful for the simultaneous distance measurement on different object planes, for measurement with uncertainty on the object-to-lens distance, and for measurement when a directional illumination and a directional observation point are required.

Due to the very small acceptance angles of telecentric lenses, only light parallel to the optical axis of the lens will contribute to the image. When a coating layer comprising reflecting platelet-shaped pigment particles is illuminated with collimated light from a first direction, and imaged with a telecentric lens having its optical axis in a second direction, only those pigment particles that are oriented in specular reflecting condition with respect to said first and said second direction will appear in the image. In other words: only those platelet-shaped pigment particles whose normal to the platelet face points into the direction of the bisector between the illumination direction and the optical axis of the telecentric lens will contribute to the image. Light rays reflected at platelet-shaped pigment particles with different orientation will not be accepted by the telecentric lens.

Figure 4A:
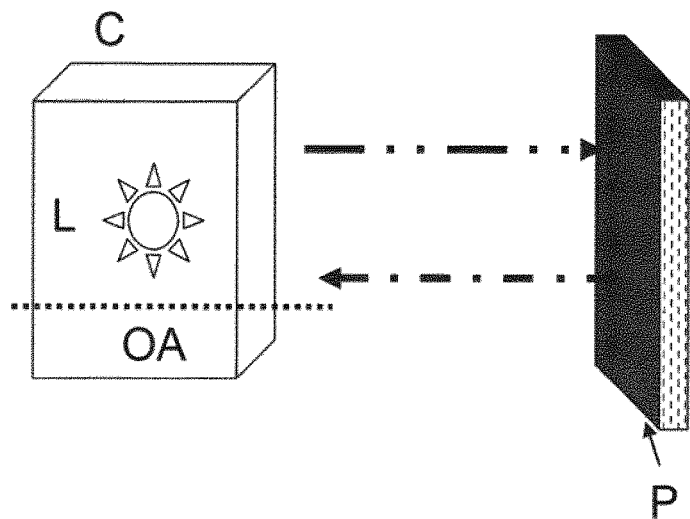
FIG. 4A schematically illustrates the light travel from an on-axis collimated light source (L) to a platelet-shaped pigment particle (P) and reflected into a telecentric lens.

If on-axis collimated light is used for the illumination of the sample (i.e., when the direction of the collimated light from light source (L) coincides with the direction of the optical axis of the telecentric lens), then only those platelet-shaped pigment particles (P) having their surface orthogonal to the optical axis of the telecentric lens will appear in the image (See FIG. 4A). Light rays reflected by platelet-shaped pigment particles whose surface is not orthogonal to the optical axis of the telecentric lens will not contribute to the image. Hence the measured light signal intensity reflected by a specimen or the image taken under such condition of said specimen comprising an OEL comprising reflecting platelet-shaped pigment particles will only reveal those of the platelet-shaped pigment particles that are in orthogonal position to the optical axis of the telecentric lens.

Figure 4B:
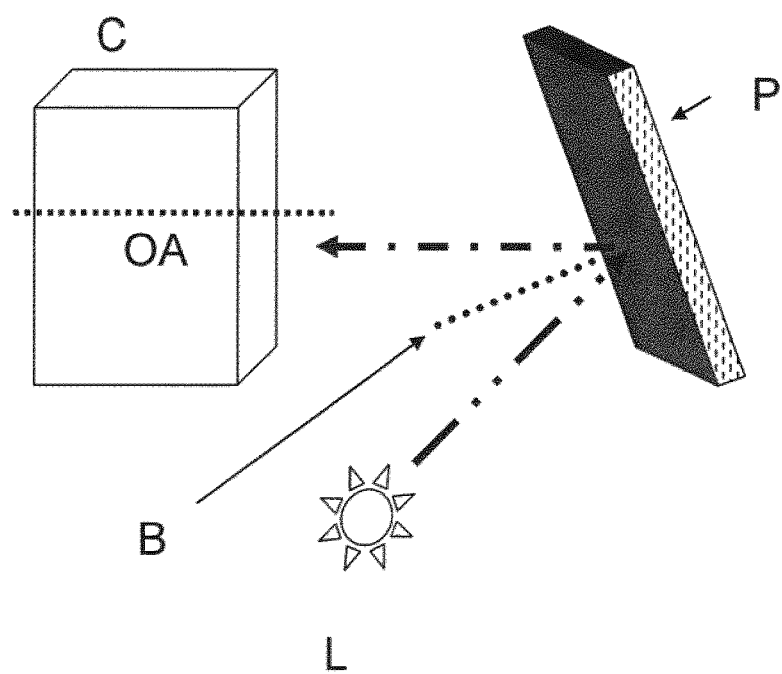
FIG. 4B schematically illustrates the light travel from an off-axis collimated light source to a platelet-shaped pigment particle (P) and reflected into a telecentric lens. The beam direction of the collimated off-axis light source is at an angle to the optical axis of the telecentric lens. The platelet-shaped pigment particle is oriented with its surface normal pointing along of the bisector (B) of said angle.

If off-axis collimated light is used for the illumination of the specimen, then the platelet-shaped pigment particles (P) having their surface perpendicular to the bisector B of the angle between the axis of the collimated light from the light source (L) and the optical axis of the telecentric lens will reflect light into the acceptance angle of the telecentric lens and contribute to the image (see FIG. 4B). Light rays reflected at pigment particles with different orientation will not be accepted by the telecentric lens, and hence, will not appear in the image (FIG. 4C).

Figure 4C:
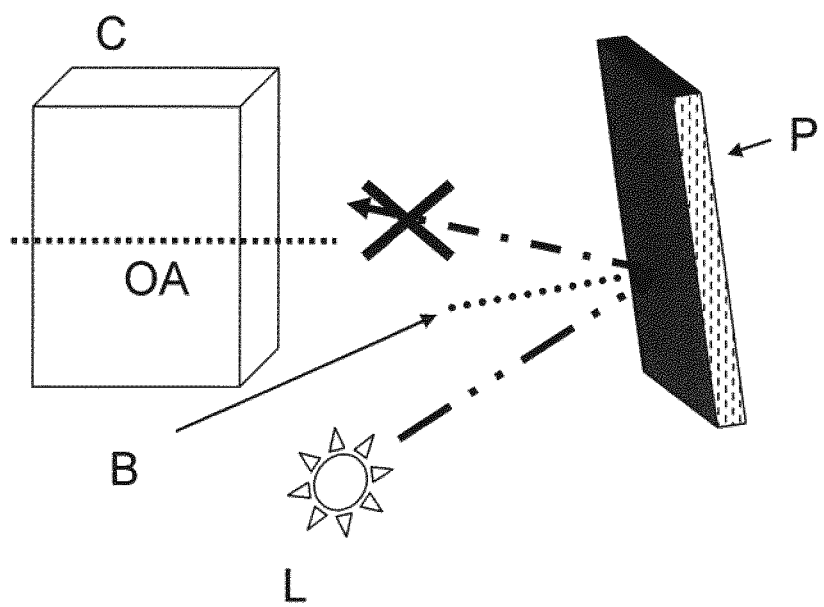
FIG. 4C schematically illustrates the light travel from an off-axis collimated light source to a platelet-shaped pigment particle (P) and reflected towards a telecentric lens. The reflected light is not aligned with the optical axis (OA) of the telecentric lens and does not contribute to the image formed on the camera (C)

If off-axis collimated light is used for the illumination of the specimen, then the platelet-shaped pigment particles (P) having their surface not perpendicular to the bisector (B) of the angle between the axis of the collimated light from the light source (L) and the optical axis (OA) of the telecentric lens might reflect light towards the telecentric lens, but this light will not pass through the telecentric lens, and hence, will not be measured by the camera (C) (FIG. 4C).

Figure 4D:
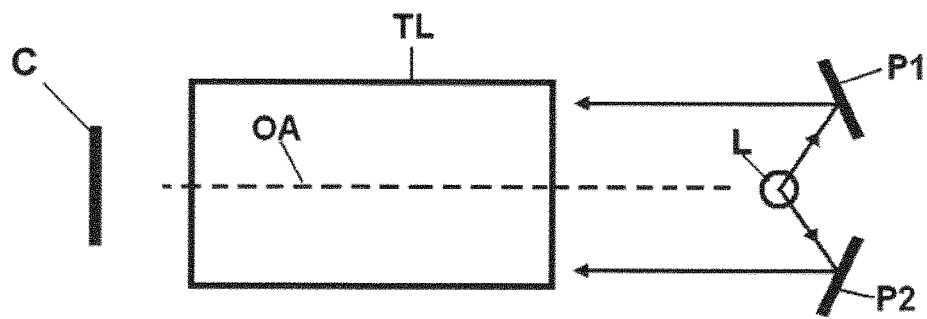
FIG. 4D schematically illustrates the light travel from an on-axis non-collimated light source towards two platelet-shaped pigment particles (P1, P2) of different orientation and back to a telecentric lens.
Figure 4E:
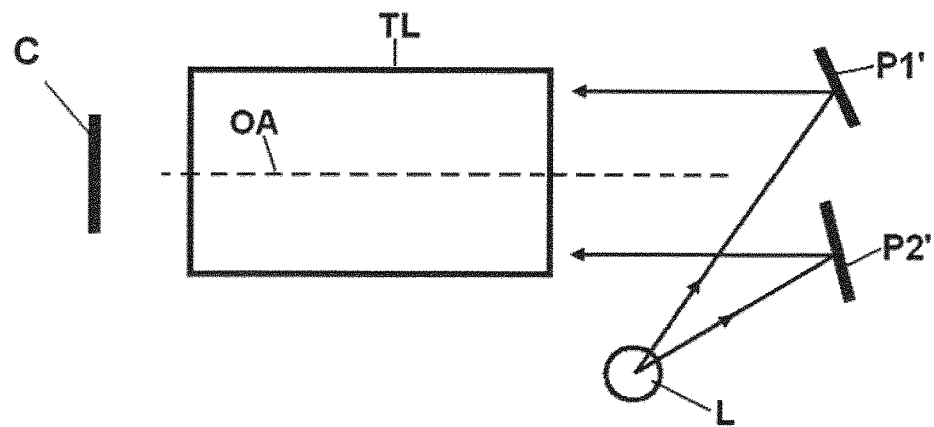
FIG. 4E schematically illustrates the light travel from an off-axis non-collimated light source towards two platelet-shaped pigment particles (P1', P2') of different orientation and back to a telecentric lens.

If non-collimated light, either on-axis or off-axis (FIGS. 4D and 4E), is used for the illumination of the specimen, nothing can be deduced about the angular orientation of the platelet-shaped pigment particles from the amount of measured light or the image obtained, because pigment particles with different orientation may reflect light rays with different orientation along the same optical axis of the telecentric lens. FIGS. 4D and 4E illustrate two platelet-shaped pigment particles (P1 and P2 or P1' and P2') of different orientation. Both pigment particles reflect light aligned with the optical axis (OA) of the telecentric lens (TL) and appear in the image.

To achieve on-axis illumination, the device must comprise an optical coupling element, to bring the collimated illuminating light beam into the axis of the optical imaging path. Such optical coupling element is preferably a beam-splitter, which may be a coupling prism or a coupling mirror. The optical coupling element may be located in front of the telecentric lens, i.e. between the front lens and the OEL to be imaged. Such arrangement has the advantage of not producing parasitic reflections in the image, but requires on the other hand large-diameter optics. In a more compact and handy optical arrangement, the optical coupling element is located inside the telecentric lens. This arrangement, however, produces parasitic reflections of the light source at the optical elements located downstream of the optical coupling element. These parasitic reflections appear in the image and must be compensated for by the subtraction of a background image comprising the parasitic reflections.

The device described herein may further advantageously comprise a specimen holder for holding said OEL in correct, focalized position, and which can be rotated in azimuth ($\alpha$) and/or elevation ($\eta$) and/or further angles with respect to the optical axis of the telecentric lens. Azimuth ($\alpha$) is herein defined as a rotation of the OEL around the y-axis (vertical axis), and elevation ($\eta$) is defined as a rotation of the OEL around the x-axis (horizontal axis) of the image plane. Since the specimen holder is operable to rotate said specimen in azimuth and/or elevation with respect to the optical axis of the telecentric lens, it allows for the exploration of the pigment particle orientation theoretically over a hemisphere. In practical application, due to the increasing defocusing at high azimuth and/or elevation angles, the angular excursion is limited to about ±50° in each direction. The specimen holder may also be a conveyor, a goniometer, or a similar arrangement by which the layer is held or placed in a defined orientation.

While rotating the specimen holder allows varying the angle of incidence and, thereby, scanning through the possible orientations of the platelet-shaped pigment particles, alternatively and instead of using a specimen holder, the collimated light source and/or the telecentric lens and/or the collector can be rotated.

Figure 5A:
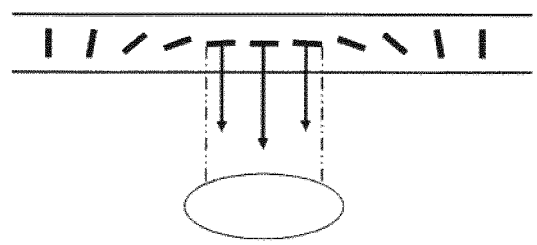
FIG. 5A schematically illustrates the on-axis light reflection at a coating composition comprising platelet-shaped pigment particles oriented such as to produce a negative "rolling bar" effect, the coating being oriented at an azimuth angle (a) of 0°. Three central pigment particles are in reflecting position.
Figure 5B:
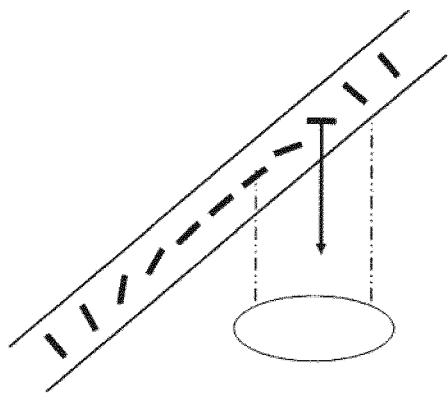
FIG. 5B schematically illustrates the on-axis light reflection at a coating composition comprising platelet-shaped pigment particles oriented such as to produce a negative "rolling bar" effect, the coating being oriented at an azimuth angle (a) of 40°. Only one lateral pigment particle is in reflecting position.

FIG. 5A illustrates the situation in which an OEL comprising a "rolling bar" effect is illuminated at a 90° angle of incidence. In this orientation, three schematically depicted platelet-shaped pigment particles are oriented such that they specularly reflect the incident light back parallel to the incoming light. FIG. 5A corresponds to an azimuth angle of 0°. FIG. 5B, on the other hand, illustrates the situation in which the OEL comprising the "rolling bar" effect is illuminated at a 50° angle of incidence. In this orientation, only one schematically depicted platelet-shaped pigment particle is oriented such that it specularly reflects the incident light back parallel to the incoming light. FIG. 5B corresponds to an azimuth angle of 40°. According to the above, there are more pigment particles reflecting light into the right direction at an azimuth angle of 0° than at an azimuth angle of 40°.

The specimen holder can comprise, alone or in combination, a rotator for further rotation axes for the specimen, as well as an angle setter for automatically setting the azimuth and/or elevation etc. angles, as well as a centerer for centering the specimen along one or more of the three space coordinates x, y, z, as well as a conveyor for automatically loading and unloading the specimen.

The device described herein may further advantageously comprise a controller, in particular a computer, for controlling the device such that a method as described above can be carried out. The controller interfaces with the device described herein, for driving the device and retrieving the image data, and may comprise software to process the image data in order to retrieve and present the platelet-shaped pigment particle orientation data from the images taken as a function of azimuth and/or elevation angle. For example, a computer can be provided, which sets the azimuth and elevation angles, as well as the angle of incident light, if applicable, activates the collimated light source, records the image of the reflected light collected by the telecentric lens, and evaluated the image data so as to extract the position and orientation of the platelet-shaped pigment particles, thus identifying positions of respectively oriented pigment particles.

In another aspect, the present disclosure provides uses of the device described herein for analytical purposes, such as the determination of the spatial distribution of platelet-shaped pigment particles over an extended region of an OEL, e.g., within a security feature based on oriented platelet-shaped optically variable magnetic or magnetizable pigment particles.

In another aspect, the present disclosure provides uses of the device described herein as a tool for the authentication of security features printed on security documents. Hence, the device may be used as a sensor device in an apparatus used for the automatic authentication of documents, such as, e.g., an ATM, for the authentication based on security features comprising oriented platelet-shaped optically variable magnetic or magnetizable pigment particles.

Hence, the device might be useful in an apparatus for the automatic authentication of documents, e.g., for the authentication of security features comprising oriented platelet-shaped optically variable magnetic or magnetizable pigment particles.

EXAMPLES

General

An example for a general setup is illustrated in FIG. 1. The setup is a "two-in-one" configuration, comprising, around a central, rotatable specimen holder, a first and a second focusable telecentric lens-and-camera assembly of different magnifications, a separate, rotatable telecentric illuminator optics and a fiber-optic illumination unit which can be plugged into each of the telecentric optical parts:

A) Telecentric Lens 1: "0.19× lens", Edmund Optics; Primary Magnification PMAG 0.19×±3%; Field of View ⅔" Sensor: 46.9 mm; working distance 120.00 mm; numerical aperture NA 0.017. The lens can be focused onto the specimen via a sliding device mounted on the instrument's ground plate.

Camera (6): Pixelink PL-B742U CMOS color (Bayer-Pattern); active area 8.57 mm×6.86 mm corresponding to 1280×1024 pixels of 6.7×6.7 μm, yielding an image area of 45 mm×36 mm and a resolution of 35×35 micrometers at the specimen surface.

B) Telecentric Lens 2: "2× lens", Edmund Optics; Primary Magnification PMAG 2.0×±3%; Field of View ⅔" Sensor: 4.4 mm; working distance 120.00 mm; numerical aperture NA 0.13 The lens can be focused onto the specimen via a sliding device mounted on the instrument's ground plate.

Camera (6'): Pixelink PL-B742U CMOS color (Bayer-Pattern); active area 8.57 mm×6.86 mm corresponding to 1280×1024 pixels of 6.7×6.7 μm, yielding an image area of 4.3 mm×3.4 mm and a resolution of 3.35 micrometers×3.35 micrometers at the specimen surface.

Depending on the desired resolution and/or the desired specimen image size, one lens or the other may be used on a same specimen; the latter can simply be turned around by 180° on the specimen holder.

The specimen holder (4) shown is one of several options; it allows azimuthal rotation of the specimen through 360°, as well as rotation of the specimen around the normal to the specimen plane.

The acceptance angle of these telecentric lenses was smaller than 2°, which allows for the selectively imaging of those platelet-shaped pigment particles oriented with their plane orthogonal, within less than two degrees, to the optical axis of the telecentric lens. Both lens-camera assemblies are shown in FIG. 1.

Light source: The illumination was provided by a Fiber-Lite® Machine Vision Illuminator DC950, 150 W Quartz Halogen Illuminator from Dolan Jenner (not depicted in FIG. 1) and a light guiding device (7 in FIG. 1).

The illumination may be provided on-axis; in this case the light guiding device is fixed directly on one of the telecentric lenses (1) or (2), which are capacitated for on-axis illumination through a built-in beam-splitter.

Alternatively, the illumination may be provided off-axis; in this case, the light guiding device is fixed into a telecentric illuminator (3) from Edmund Optics. The telecentric illuminator (3) is mounted on a rotatable platform (5), allowing it to be azimuthally rotated with respect to telecentric lenses (1) and (2). The optical axes of telecentric lenses (1) and (2), and of telecentric illuminator (3) cross at a common point of the instrument.

Collector (camera 6, 6'): Photographic imaging was performed by two already mentioned 1.3 MPixel CMOS cameras PixeLINK™ PL-B742 USB 2.0 from Edmund Optics Ltd.; Active sensor area (⅔"); Resolution 1280×1024 pixels; Pixel size: 6.7 μm×6.7 μm. The CMOS cameras (1), (2) were mounted on the telecentric lenses (6), (6'), respectively. CMOS cameras were preferred to CCD cameras as the image sensors, because of their higher linearity at strong light intensity and their lower sensitivity to blooming effects.

A rotatable specimen holder (4) comprising a vertical plate was positioned at the optical center of the instrument, such that its vertical rotation axis crosses the optical axes of the telecentric optical elements (1), (2) and (3). An azimuth angle of 0° corresponds to a specimen position on the sample holder (4) where the sample faces the telecentric lens (1); at an azimuth angle of 180°, the specimen on the holder faces the telecentric lens (2), its surface plane being then perpendicular to the optical axes of the telecentric lenses (1, 2). The device further preferably comprises a rotator (5) such as, for example, a rotation gear for the rotation of the specimen around the normal to the specimen plane.

Specimen images taken at specular conditions, i.e. at conditions where the normal to the plane of the specimen, i.e., the OEL, points into the direction of the bisector of the illumination direction and the optical axis of the telecentric lens—in case of on-axis illumination where the normal to the plane of the specimen points in the direction of the optical axis of the telecentric lens—are not useful because of the intense specular reflection component present from the more or less glossy specimen surface.

The images are preferably taken with background correction. This means that a background image, accounting for dark current effects in the photosensor (CMOS or CCD camera) and, in case of on-axis illumination, for back-reflected light from the optical elements ahead of the beam-splitter, is subtracted from each of the images. The image subtraction is preferably performed electronically and pixelwise.

The background image to be subtracted is obtained using the same illumination and photographic exposure conditions as used for taking the image, but with a perfectly dark target in place of the specimen.

The background image can, e.g., be taken by having the cover of the telecentric lens closed, given that the interior of said cover is perfectly dark. Another way to obtain a background image is to take the image of a dark, optically flat glass plate in place of the specimen, oriented at a non-specular angle in a dark environment; in this way, incident light reflected at the surface of the glass plate is directed away from the telecentric lens, and incident light penetrating the dark glass plate is absorbed.

Figure 2A:
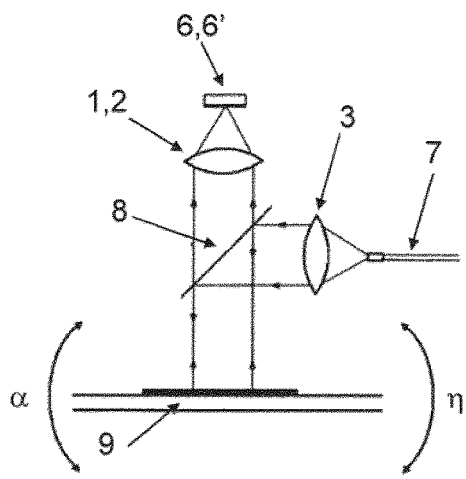
FIG. 2A schematically illustrates the working principle of a device of the present disclosure with on-axis illumination with collimated light.
Figure 2B:
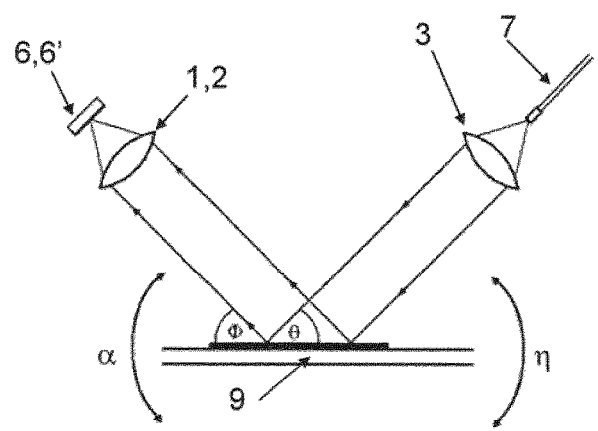
FIG. 2B schematically illustrates the working principle of a device of the present disclosure with off-axis illumination with collimated light.

In FIGS. 2A and 2B, the working principles of two setups for telecentric imaging of viewing angle dependent features are illustrated. FIG. 2A illustrates the working principle for an on-axis collimated illumination instrument. A fiberoptic illuminator (7) is provided as the light source, and the light emitted from this illuminator is collimated by a condenser lens (3) acting as the collimator. A semi-transparent coupling mirror (beam splitter) (8) directs part of the collimated light from the condenser lens (3) onto a specimen surface, i.e., an OEL. The incident light reflected at the pigment particles comprised in the OEL passes through the coupling mirror (8) and through a telecentric lens (1,2), which forms a two-dimensional image of the specimen surface on the CCD camera, acting as a collector (6, 6'). The telecentric lens limits the image to light components that are substantially parallel to its optical axis. Therefore, only pigment particles in or on the specimen surface that have a reflecting plane orthogonal to the optical axis of the telecentric lens appear in the image. In order to gain insight into the distribution of pigment particles of different orientations, the specimen is placed on a rotatable holder that can be inclined about two independent axes with respect to the optical axis of the telecentric lens, and thereby allows one to systematically rotate pigment particles of any orientation into reflecting position. In practical application, the telecentric lens may not be a single lens, but an assembly of many optical elements. The semitransparent coupling mirror is placed in front of this assembly, or somewhere inside this assembly, and provides the advantage of a more compact optical unit, but has the disadvantage of contaminating the image with parasitic light reflections from the optical elements located ahead of the coupling mirror.

Similarly, FIG. 2B schematically illustrates an example of an off-axis collimated illumination instrument. The optics of this second setup are basically identical to those of the above described setup illustrated in FIG. 2A, with the exception that the collimated illumination is now directly provided onto the specimen surface under a first angle θ to said specimen surface, without going over a coupling mirror. The optical axis of the telecentric lens-and-camera assembly is oriented at a second angle Φ to said specimen surface. Only those pigment particles in or on the specimen surface that have a reflecting surface, whose normal is oriented in the direction of the bisector of the illumination direction and the optical axis of the telecentric lens, reflect light into the acceptance angle of telecentric lens, thus contributing to the image formed in the camera.

Example 1

Figure 6A:
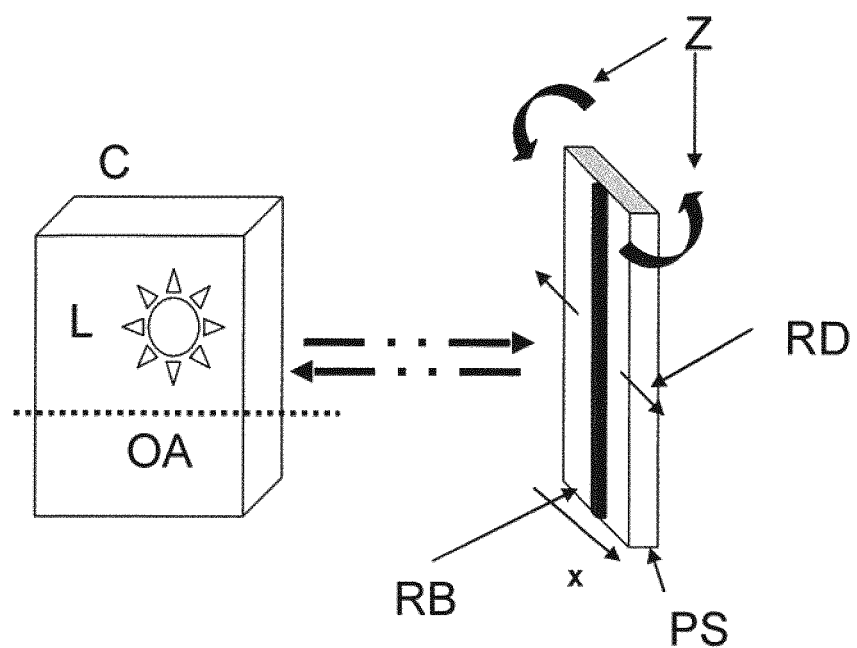
FIG. 6A schematically illustrates a setup as used for Example 1.

A) As schematically illustrated in FIG. 6A, a specimen PS was printed with a UV-curable ink comprising platelet-shaped green-to-blue optically variable magnetic pigment particles (diameter d50 about 15 µm and thickness about 1 µm, obtained from JDS-Uniphase, Santa Rosa, Calif.). An OEL was produced through the application of a magnetic field generating device thereby orienting platelet-shaped optically variable magnetic or magnetizable pigment particles according to a dynamic optically variable effect known as the "rolling bar" RB as disclosed in US 2005/0106367 A1. The orientation of the platelet-shaped optically variable magnetic or magnetizable pigment particles was frozen by UV-irradiation of the specimen.

B) The specimen was placed on the vertically rotatable specimen holder of the instrument of FIG. 1 a, in "vertical position" with "horizontal rolling direction" RD of the "rolling bar", i.e. the "rolling bar" appeared in vertical position and was horizontally left-right moving along the x-axis of the specimen surface when the azimuth angle Z of the rotatable specimen holder was varied.

Figure 6B:
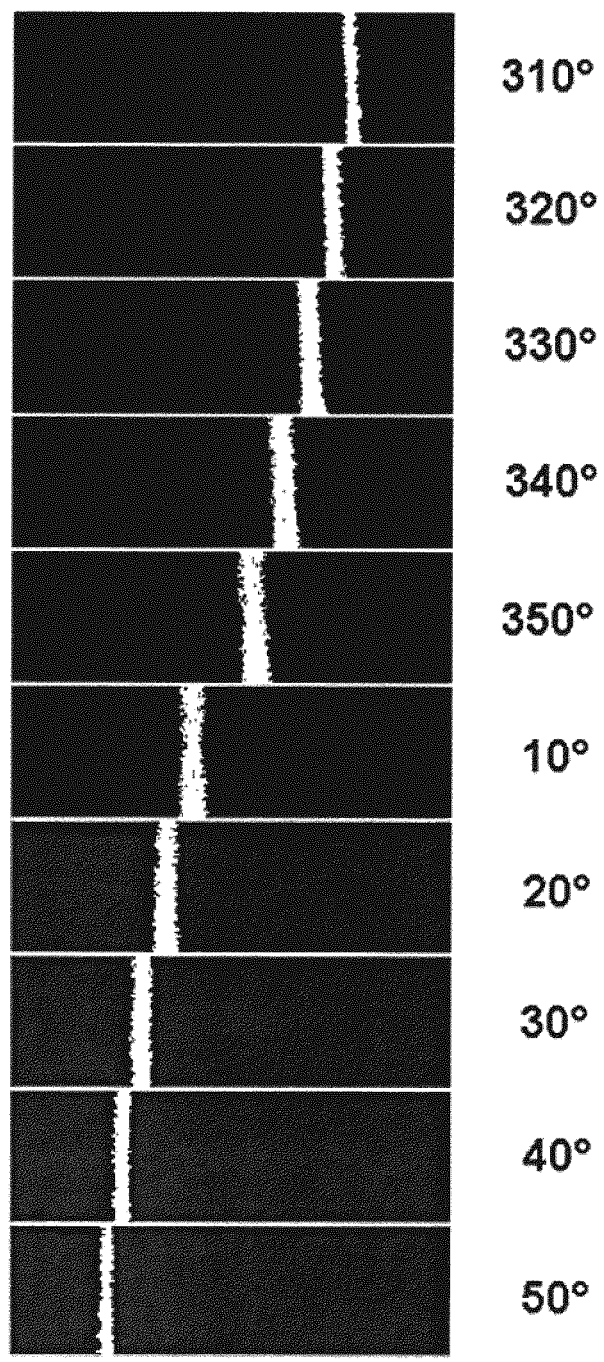
FIG. 6B represents a series of pictures captured at different azimuth angles of the specimen as measured for Example 1.

C) The specimen was illuminated with an on-axis collimated light source fixed on the telecentric lens 1 in FIG. 1 (primary Magnification PMAG 0.19×±3% described hereabove). The azimuth angle of the specimen holder 4 was varied from (−50°=310°) to)(+50° in 10° steps. At each azimuth angle, except for 0°, a digital image of the specimen was captured and recorded on a computer. Each of these images showed a light band corresponding to the position of the "rolling bar", displacing along the x-axis of the specimen surface as a function of the viewing-angle (FIG. 6B).

D) The amount of reflected light passing through the telecentric lens 1 was measured with a CCD camera, C in FIGS. 6A and 6, 6' in FIG. 1, (PixeLINK™ USB 2.0 CMOS camera). The registered data were analyzed with the publically available platform for image analysis Fiji (also described in Nature Methods 9(7): 676-682). The images were corrected for background effects by pixelwise subtracting the background image from each of them, by using Fiji's "Process-Image calculator" function, and x-scaled by a factor f of $1/\cos(\alpha)$ using Fiji's "Image-Scale" function, in order to compensate for perspective distortion (Lambert factor), as follows:

| Azimuth Angle | Factor f |
| --- | --- |
| ±10° | 1.015 |
| ±20° | 1.064 |
| ±30° | 1.155 |
| ±40° | 1.305 |
| ±50° | 1.556 |

The scaled images were put onto a Fiji image stack, horizontally aligned according to an image internal reference point using Fiji's "Align Slice" plug-in and the image stack was cropped to a size of 300×300 pixels comprising the central part of the moving "rolling bar" reflection. The individual images of the so cropped image stack have now a same origin and metric, and were retained as the primary measurement result.

Figure 7:
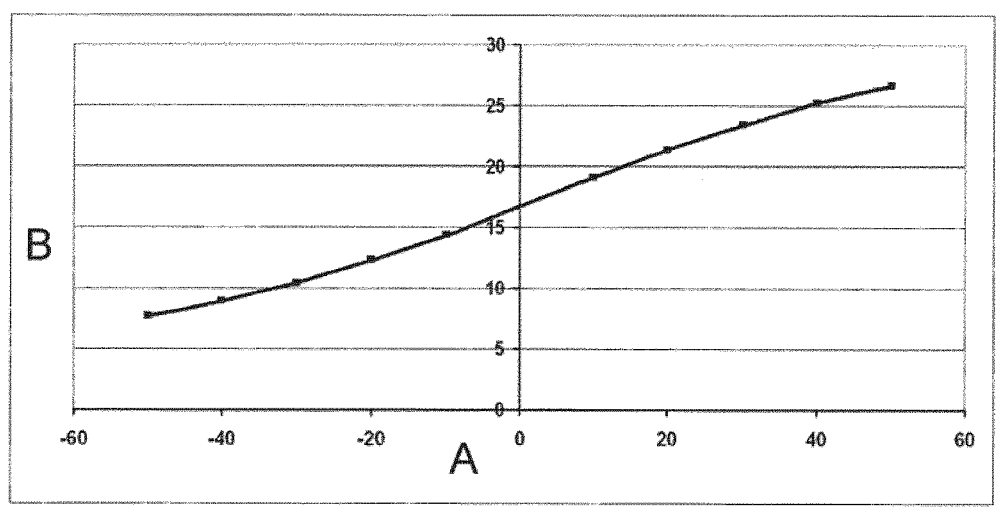
FIG. 7 is a diagram of a variation of the position of the center of a rolling bar depending on an azimuth angle.

E) From the primary measurement result, the positions of the "rolling bar" reflections as a function of the azimuth angle (viewing angle) were evaluated (FIG. 6B; FIG. 7).

In the following, Gaussian profiles of the form $I=I_0*\exp\{-(\frac{1}{2})*(x-x_0)^2/d^2\}$ were fitted to the reflection intensity distributions across the "rolling bar", taking into account that with the used 0.19× lens, 1 pixel in the image corresponds to 0.035 mm (35 µm) on the specimen surface. The three values $I_0$, $x_0$, and d are thus obtained from each image. The $x_0$-position of the "rolling bar" can also be obtained by simply determining the center of the clear zones in FIG. 6B. FIG. 6B illustrates the images collected by the CMOS type camera at angles of 310°, 320°, 330°, 340°, 350°, 10°, 20°, 30°, 40° and 50°.

FIG. 7 shows the variation of the position $x_0$ of the center of the "rolling bar" (B in mm) along the x-axis of the specimen according to the azimuth angles (A in degree).

Figure 8:
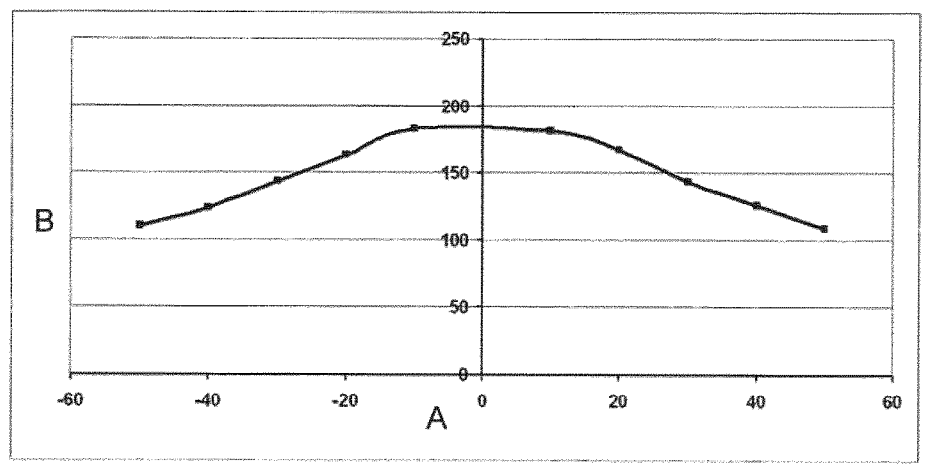
FIG. 8 is a diagram illustrating a variation of the intensity of the total reflected light of the rolling bar depending on an azimuth angle.

FIG. 8 shows the variation of the intensity $I_0$ (B, a.u.) of the total reflected light of the "rolling bar" as a function of the azimuth angles (A in degree). The intensity values can be interpreted as a measure of the total amount of light-reflecting surface in a given direction, i.e. a given azimuth angle. This may indicate the amount of pigment particles oriented to reflect at this azimuth angle.

Figure 9:
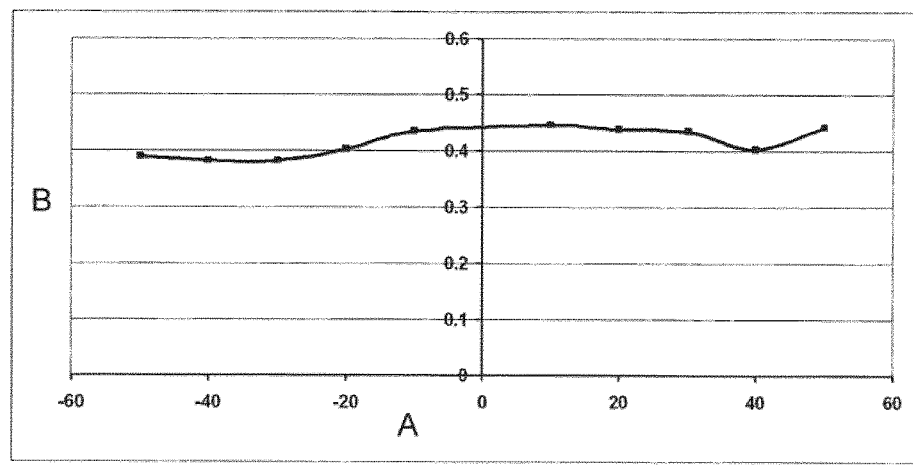
FIG. 9 is a diagram showing a variation of a standard deviation of fitted Gaussian distributions of the reflected light intensity depending on an azimuth angle.

FIG. 9. shows the variation of the factor d (standard deviation, B in mm) of the fitted Gaussian distributions of reflected light intensity, plotted as a function of the azimuth angle (A in degree). The approximate azimuth angle independence of the d-value might indicate that the "rolling bar" has a constant width at all azimuth angles.

Example 2

The same specimen was used as for Example 1.

Figure 6C:
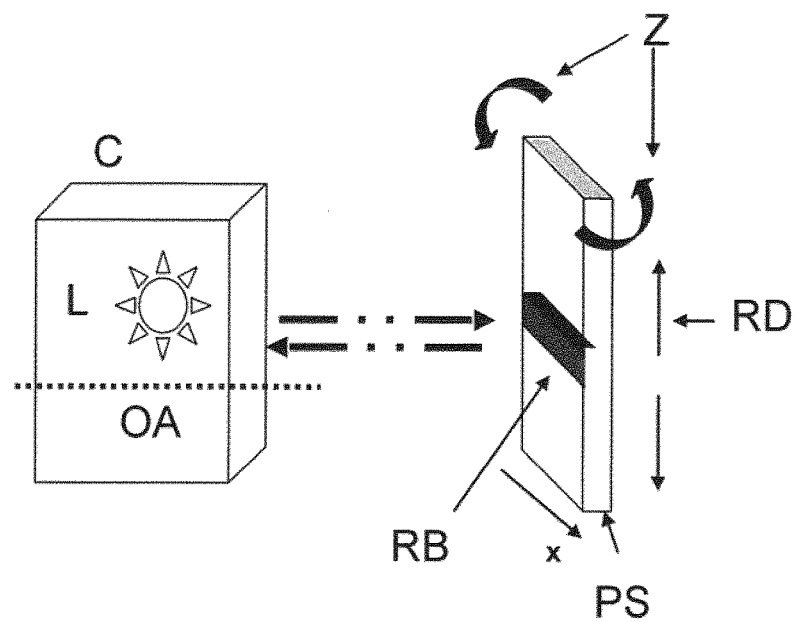
FIG. 6C schematically illustrates a setup as used for Example 2.

B) The specimen was now placed on the vertically rotatable specimen holder of the instrument of FIG. 1, in "horizontal position" i.e. the "rolling bar" appeared in horizontal position and no horizontal left-right moving along the x-axis of the specimen surface was observed when the azimuth angle Z of the rotatable specimen holder was varied. The situation is illustrated in FIG. 6C.

Steps C) and D) were performed as for Example 1.

E) From the primary measurement result, the intensity of the "rolling bar" reflection was evaluated as a function of the azimuth angle (viewing angle). The "rolling bar" did not move in the orientation of Example 2, but only changed intensity in function of the viewing angle. The total reflection intensity was obtained for each image, by integrating the clear part of the image surface.

Figure 10:
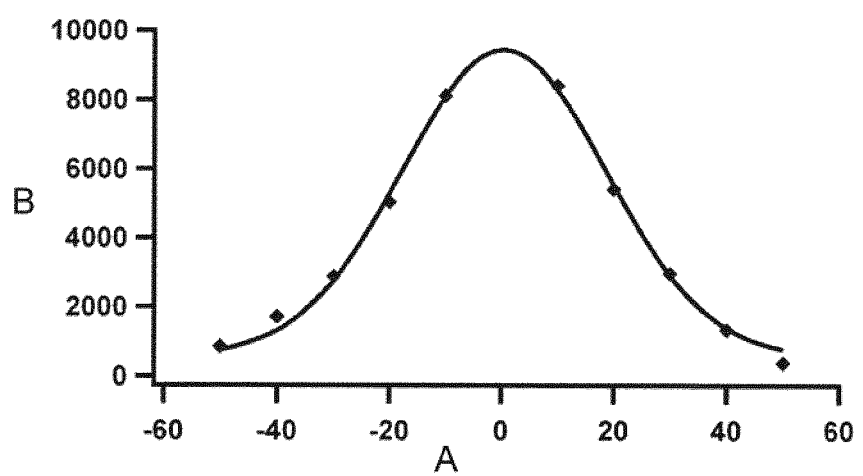
FIG. 10 is a further diagram which illustrates reflected light intensities depending on an azimuth angle.

FIG. 10 shows the reflected light intensities (B, a.u.) as a function the azimuth angle (A in degree) (viewing angle); a bell-shaped curve is observed. The intensity values can be interpreted as a measure of the total amount of light-reflecting surface in a given direction, i.e. a given azimuth angle. This may indicate the amount of pigment particles oriented to reflect at this azimuth angle.

A Gaussian evaluation of the reflection intensity as a function of the azimuth angle gave a reasonable fit. The reflection intensity follows, indeed a Gauss distribution, centered at the origin, and having a standard deviation of roughly 18°. This can be interpreted as the deviation of the pigment particles from flat alignment with the substrate plane.

The invention claimed is:

1. A method for determining a distribution and orientation of platelet-shaped pigment particles over an extended region of an optical effect layer comprising said pigment particles, the method comprising:
    a) taking at least one image, under illumination of said extended region of the optical effect layer with collimated light incident from at least one first direction, of reflected light of said extended region of the optical effect layer from at least one second direction, by using a telecentric lens-and-camera assembly having the optical axis of the telecentric lens oriented along said second direction, and
    b) processing the at least one image of said extended region to extract quantitative particle distribution and orientation information.

2. The method of claim 1, wherein said second direction is the same as said first direction.

3. The method of claim 1, further comprising c) tilting the optical effect layer with respect to the first orientation so that the plane of said extended region of the optical effect layer is rotated in azimuth and/or elevation with respect to the optical axis of the telecentric lens, wherein a) and b) are carried out after the optical effect layer being tilted.

4. The method of claim 3, wherein the c) tilting the optical effect layer is carried out successively a plurality of times.

5. The method claim 1, further comprising determining a position or coordinate of a maximum intensity of the collected light.

6. The method of claim 1, further comprising integrating an intensity of the collected light over the collected light.

7. The method claim 1, wherein the b) processing the at least one image of said extended region comprises an intensity-filtering of the at least one image or a color-filtering of the at least one image.

8. The method of claim 1, further comprising compensating the locally resolved intensity of the collected light for perspective distortion.

9. The method according claim 5, wherein the c) processing the at least one image of said extended region comprises 1-dimensional or 2-dimensional curve fitting to an image feature.

10. A device for determining a distribution and orientation of platelet-shaped pigment particles over an extended region of an optical effect layer comprising said pigment particles, the device comprising:
    a) a collimated light source for illuminating an extended region of the optical effect layer with collimated light from at least one first direction,
    b) a telecentric lens-and-camera assembly for collecting the light reflected from said extended region of the optical effect layer into at least one second direction, wherein an optical axis of the telecentric lens-and-camera assembly is oriented along said second direction and the telecentric lens-and-camera assembly is configured for taking at least one image, under illumination of the extended region of the optical effect layer with the collimated light incident from the first direction, of the light reflected from the extended region of the optical effect layer from the second direction, and
    c) a processor for processing the at least one image of the extended region to extract quantitative particle distribution and orientation information.

11. The device of claim 10, wherein the telecentric lens of the telecentric lens-and-camera assembly is equipped with an on-axis illuminator, for illuminating and taking the image from the same direction.

12. The device of claim 10, wherein the camera of the telecentric lens-and-camera assembly is a CMOS type camera or a CCD type camera.

13. The device of claim 10, further comprising a specimen holder for holding said optical effect layer, wherein the specimen holder is rotatable in azimuth and/or elevation with respect to the optical axis of the telecentric lens.

14. The device of claim 10, further comprising a controller configured for driving the device and retrieving image data, such that the method of claim 1 can be carried out.

15. Use of the device according to claim 10 for carrying out a method for determining the distribution and orientation of platelet-shaped pigment particles over the extended region of the optical effect layer.

16. The method of claim 2, wherein said second direction being the same as said first direction is achieved using a telecentric lens with on-axis illuminator.

17. The method claim 5, wherein the position or coordinate of the maximum intensity of the collected light is set in relation to the orientation of the optical effect layer when the light was collected.

18. The method of claim 6, wherein the integrated light intensity of the collected light is set in relation to the orientation of the optical effect layer when the light was collected.

19. The method of claim 8, wherein the locally resolved intensity of the collected light is compensated for perspective distortion depending on an angle of the second direction, along which the reflected light travels, towards the orientation of the optical effect layer.

20. The device of claim 10, wherein the device is operable to perform the method of claim 1.

21. The device of claim 14, wherein the controller is a computer.

* * * * *